United States Patent [19]

Shutt

[11] Patent Number: 4,830,000

[45] Date of Patent: May 16, 1989

[54] SURGICAL DRILL

[75] Inventor: George V. Shutt, Glendora, Calif.

[73] Assignee: Aspen Laboratories, Inc., Greenwood Village, Colo.

[21] Appl. No.: 140,288

[22] Filed: Dec. 31, 1987

[51] Int. Cl.⁴ .................. A61B 17/32; A61B 39/10
[52] U.S. Cl. .................. 128/305.1; 128/310; 408/225; 408/230; 408/207
[58] Field of Search .............. 128/305.1, 3.0; 408/230, 229, 225, 715, 207, 59

[56] References Cited

U.S. PATENT DOCUMENTS 41,517   3/1864  Low .
277,966  2/1883  Whiteside .
2,675,003 1/1954 Veley ................. 128/310
3,076,356 4/1960 Simich ................. 77/67
3,779,664 12/1973 Caley et al. ........... 408/230 X
3,836,278 4/1974 McInnes ............... 408/199
4,341,206 1/1982 Perrett et al. .......... 128/92

Primary Examiner—Stephen C. Pellegrino
Attorney, Agent, or Firm—Paul David Schoenle

[57] ABSTRACT

A drill includes a plurality of lips with enlarged portions at one end defining heads therefore. The heads form frusto-conical surfaces and cutting edges extend from the frusto-conical surfaces to remove chips. The cutting edges are limited in size with respect to the frusto-conical surfaces to control the removal of chips and a pocket behind each head readily receives the shavings to convey the latter away from the one end.

9 Claims, 2 Drawing Sheets

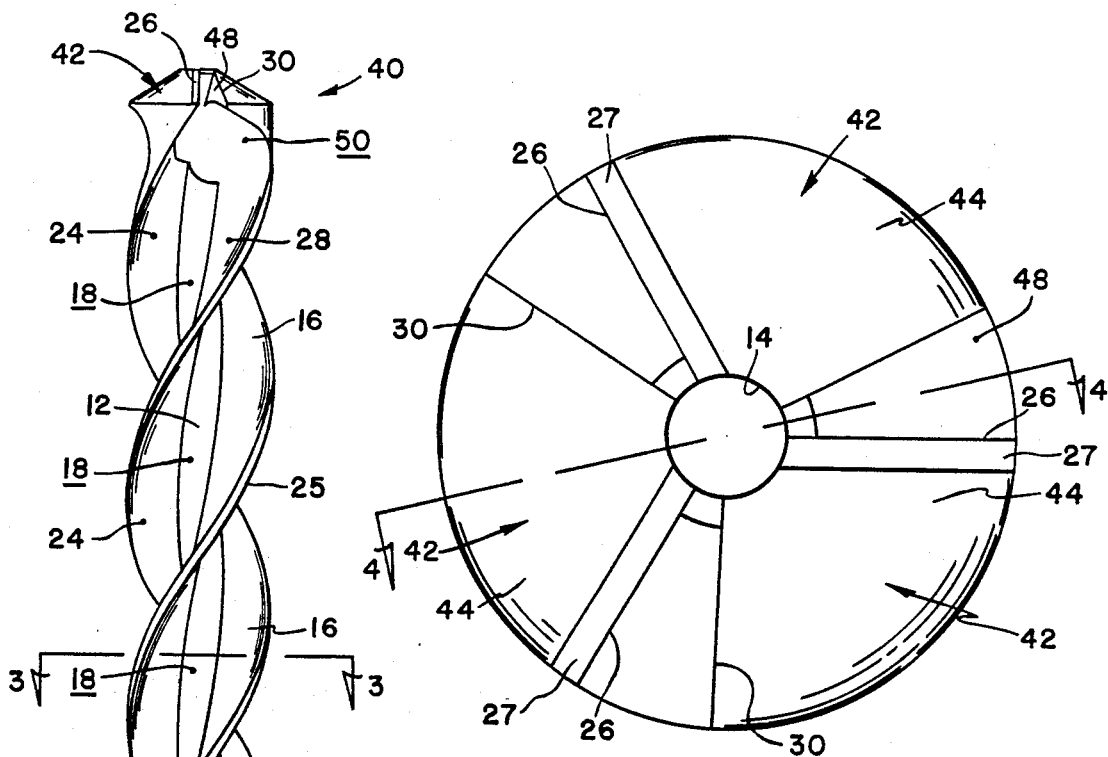
FIG. 2
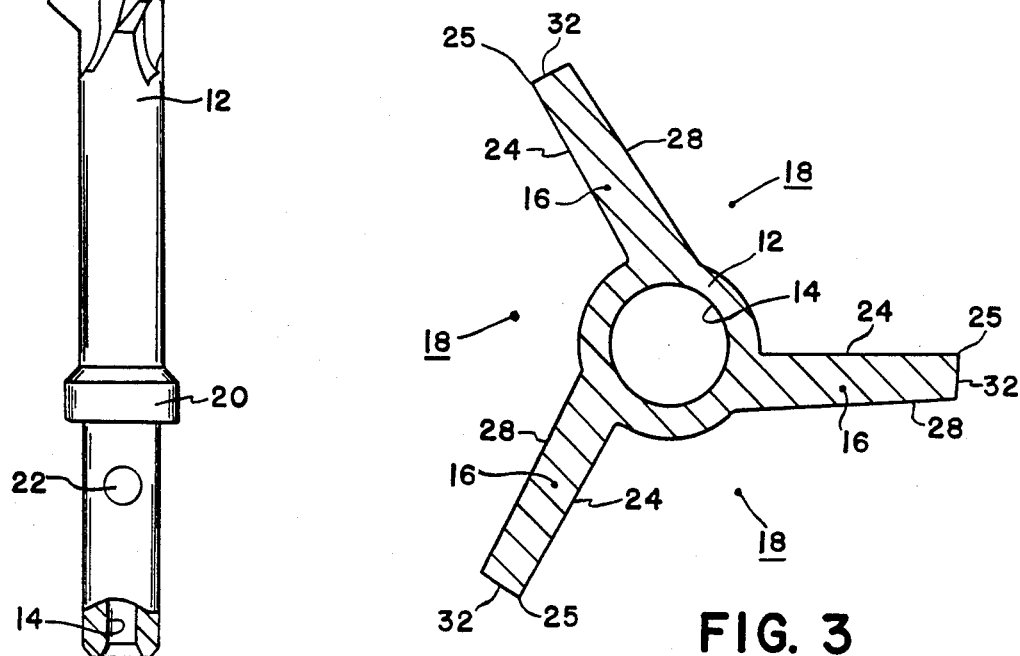
FIG. 1
FIG. 3

SURGICAL DRILL

The present invention relates to a surgical drill for generating a hole in a bone.

Drilling into a bone for anterior cruciate ligament replacement, among other orthopaedic applications, involves drilling into and breaking out of an angulated non-flat surface relative to the drill's axis. More often the case than not, the breakout is at a location on the bone which is substantially contoured and generally oriented at angles as great as 45° from the drill axis. If a drill/reamer for such application has a shallow helix/rake angle and numerous lips, feeding of the bone shavings or chips is hampered with the result that the flutes are jammed and the force required for drilling is increased with undesirable heat build up. Although reducing the number of flutes results in greater flute area, little, if any, advantage in shaving flow is obtained. Moreover, reducing the number of flutes increases the risk of sudden grabbing and breakage of the drill and/or bone at breakout. With the flutes jammed by bone shavings, due to the higher force required to advance the drill, the drill will tend to break through the exit area rapidly and damage bone stock at such area, as well as causing the drill to hit another surface resulting in unacceptable trauma. The potential for damage is further compounded with a hand-held tool controlling the drill, as the rate of travel is difficult to control at breakout. When the drill breaks partially through the bone, the remaining portion of the drill will catch a lip on the partial opening of the bone and corkscrew uncontrollable with damage to the exit area and other surfaces resulting. Such forces on the drill may also increase the danger of over stressing the drill and breaking the same within the bone.

The present invention provides a surgical drill which is designed to accommodate the combined requirements of cutting, breakout control, stress control and shaving removal. A high helix and high rake angle provide for easy shaving of bone with diminished compaction of the shavings within spiral flutes. A substantially closed tip captures the shavings to more readily pull them back from the tip and minimize shavings falling out into the exit area. The exit area for anterior cruciate ligament replacement is within the knee joint. The tip design controls penetration and breakout speed with a frusto-conical surface having no angular relief. Cutting edges protrude from the frusto-conical surface on a small portion thereof so that a proportionally large "dead" surface on the frusto-conical surface does not cut.

It is an object of the present invention to drill a hole in a bone with adequate shaving removal away from the tip as well as controlled breakout to reduce the potential for corkscrewing of the drill at the exit area and to avoid generating excessive heat.

In the drawings,

FIG. 1 is a side view of the surgical drill of the present invention,

FIG. 2 is a left end view of FIG. 1,

FIG. 3 is a cross-section view taken along line 3—3 of FIG. 1,

Figure 4:
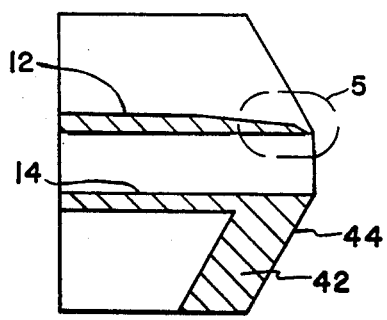
FIG. 4 is a cross-section view taken along line 4—4 of FIG. 2.
Figure 5:
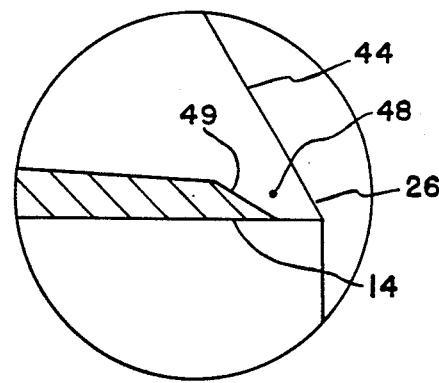
FIG. 5 is an enlarged view of the circumscribed portion 5 of FIG. 4.

A surgical drill 10 includes a tubular shank 12 with an opening 14 extending therethrough to define a longitudinal axis for the cannulated drill. A plurality of lips 16, preferably three in number, extend radially outwardly from the tubular shank 12 to form a helix pattern with a spiral flute 18 between each lip. A flange 20 cooperates with a detent 22 at the attachment end to accommodate disposition of the drill 10 within a chuck of a drill motor (not shown). Each spiral lip includes one side wall 24 leading to a cutting ridge 25 and an opposite side wall 28. An outer ridge 32 on each lip connects the walls 24 and 28 and the walls 24 and 28 extend longitudinally to terminate in a cutting edge 26 and a tail 30 at a cutting end or tip 40 of the drill.

Figure 6:
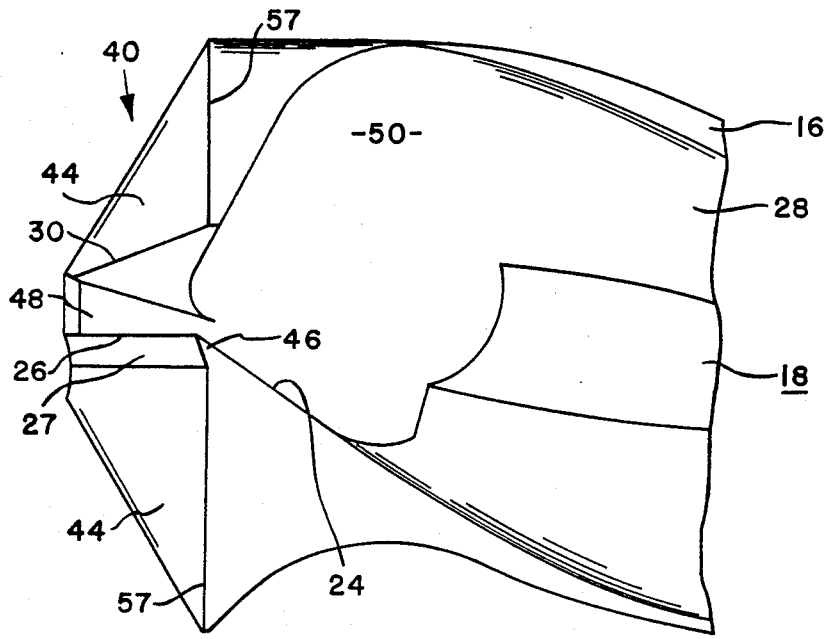
FIG. 6 is an enlarged view of the left end of FIG. 1.

Turning to FIGS. 2 and 6, the cutting end or tip 40 of the drill includes a head 42 for each lip. Each head 42 defines a frusto-conical surface 44 with the cutting edge 26 protruding slightly therefrom by means of a slight protrusion 46. Each head 42 extends arcuately about the drill longitudinal axis at the tip 40 to substantially close the tip. Each head forms an angle of about 95° so that 285° of the circular tip is formed by the three flute heads. Adjacent heads cooperate to form gaps 48 between the cutting edges 26 and the tails 30. Each gap forms a small angle so that substantially 50% to 80% of the tip is closed by the heads 42. In one embodiment, the head forms a 95° angle and the gap forms a 25° angle. In addition, the slight angular protrusion 46 forming the cutting edges 26 is confined to a radially extending narrow strip 27 adjacent the walls 24 of the heads 42, so that most of the cutting tip 40 provides a "dead" surface not capable of generating bone shavings and controlling the "feed" rate of foreward movement.

Figure 7:
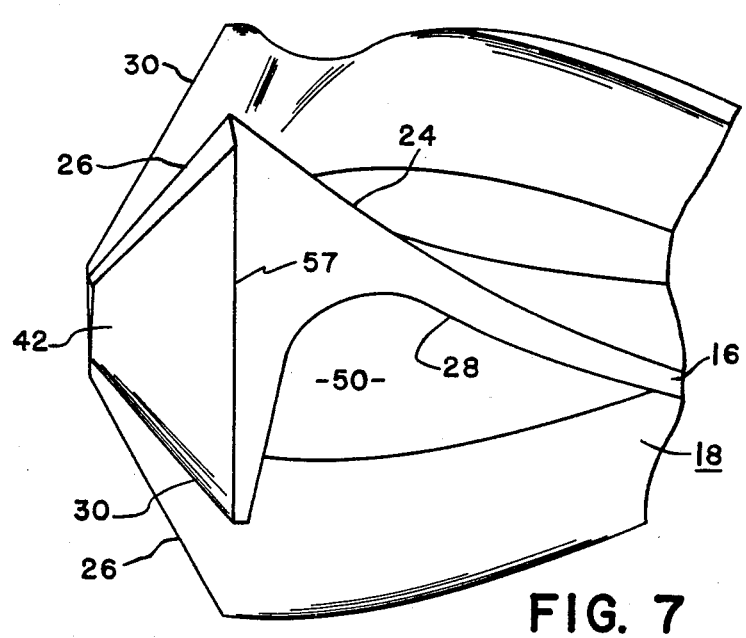
FIG. 7 is a view similar to FIG. 6 with the drill rotated to fully illustrate a side view of a flute head.

As shown in FIG. 6, the one side wall 24 of each flute 16 extends uniformly, without any abrupt change in direction, toward the frusto-conical surface to form the cutting edge 26. In contrast thereto, the opposite side wall 28 of each lip 16 makes an abrupt change in direction at the head 42 to intersect the tail 30 and form a pocket 50 immediately behind the head in direct communication with the gap 48 and trough 18. Viewing FIGS. 6 and 7, the frusto-conical surface terminates at an outer boundary 57 and the boundaries for each head 42 coincide with a plane orientated in a normal direction to the longitudinal axis.

The surgical drill described and illustrated herein provides for controlled removal of bone shavings as the cutting edges protrude from frusto-conical surfaces which comprise a major portion of the drill tip in contact with that portion of bone to be removed. Moreover, the frusto-conical surfaces are orientated with their center axes coinciding with each other and with the longitudinal axis so that these surfaces do not "bite" into the bone. In addition, the bone shavings are readily conveyed by the high helix in response to rotation of the drill. When the part of the drill tip begins to breakout, the frusto-conical surfaces continue to limit the amount of bone removal, preventing "corkscrewing" so that the drill does not instantaneously advance outwardly at the breakout site and damage bone or other tissue. As the drill is removing bone shavings at the breakout site, the gap and pocket cooperate to capture bone shavings so that minimal bone shavings, if any, will fall out at the breakout exit hole.

In addition, the aforegoing surgical drill provides flutes and gaps of sufficient size to permit easy cleaning of the drill following surgery. Since bone shavings are similar to putty, it is desireable to provide a high helix with adequate flute openings for the bone shaving removal during cleaning of this drill.

In the preferred embodiment the cutting edge is about 0.005 inches (0.125 mm) above the frusto-conical surfaces. The helix angle for the flutes is about 30° from the longitudinal axis and the frusto-conical surfaces form about a 60° angle with respect to the longitudinal axis. In cross section, the one side wall 24 defines a straight line, see FIG. 3, which can be projected radially inwardly to intersect the longitudinal axis.

I claim:

1. A drill for generating a hole comprising a shank defining a longitudinal axis, a plurality of lips extending radially outwardly from the shank and extending longitudinally in a spiral pattern to form flutes between consecutive lips, each of the flutes defining one side leading to a cutting edge and an opposite side leading to a tail, the one side and opposite side of adjacent flutes cooperating to define a spiral flute therebetween leading to a gap adjacent the cutting edge for the passage of shavings away from the cutting edge during drilling, each lip including a head at one end defining the cutting edge and the tail therefore, the head forming a substantially frusto-conical surface between the cutting edge and the tail, the cutting edge generating shavings during drilling, and the opposite side of each flute at the head extending from the tail toward the associated head cutting edge to substantially form a pocket within the flute for receiving the shavings during drilling in order to readily convey the shavings away from the head as the drill is rotating and generating the shavings.

2. The drill of claim 1 in which the tail of one flute cooperate with the cutting edge of an adjacent flute to form a gap therebetween leading to the pocket and the pocket forms a width substantially wider than a width for the gap.

3. The drill of claim 2 in which the opposite side of the one flute and the one side of the adjacent flute extend away from the gap in opposite directions at the corresponding heads therefore to provide for a substantial increase in the area provided for removing the shavings from the gap to the flute in close proximity to the cutting edge.

4. The drill of claim 1 in which each substantially frusto-conical surface includes a boundary at the outer radial dimension therefore and all of the boundaries coincide with a plane normal to the longitudinal axis.

5. The surgical drill of claim 1 in which the plurality of lips define a helix angle with respect to the longitudinal axis and the opposite side of each lip at each head extends in a normal direction to the helix angle in order to dispose the pocket closely behind the frusto-conical surface in close proximity to the cutting edge.

6. The drill of claim 1 in which the plurality of flutes comprises three flutes with three frusto-conical surfaces defining the cutting edges and the tails, the three frusto-conical surfaces each extending circumferentially about the longitudinal axis to define an arc of about 60° to 95° and each gap defines an arc of about 25° to 60° so that the frusto-conical surfaces cover an area equal to or larger than the gaps.

7. The drill of claim 1 in which the cutting edges are formed by small angular protrusions extending outwardly from the frusto-conical surfaces and the protrusions are substantially smaller in surface area than the frusto-conical surfaces surface area.

8. A drill for generating a hole in a bone comprising a shank with a longitudinal axis, a plurality of lips extending in a spiral pattern along the shank to form spiral flutes, each lip including a cutting edge and a tail at one end of the drill, each lip defining a head at the one end with an enlarged width for the flute to form a frusto-conical surface between the cutting edge and the tail, each frusto-conical surface including the same axis of rotation which is coincident with the longitudinal axis so that only the cutting edge is utilized to remove bone chips during drilling, the cutting edge being formed by a protrusion extending beyond each frusto-conical surface, and each head forms a pocket adjacent the tail and directly behind each frusto-conical surface in direct communication with one of the flutes to provide for removal of bone shavings generated by the cutting edge during drilling.

9. The surgical drill of claim 8 in which the shank, the lips, and the heads comprise a one-piece integral part.

* * * * *